United States Patent
Zhang et al.

(10) Patent No.: US 10,881,636 B2
(45) Date of Patent: Jan. 5, 2021

(54) DIHYDROARTEMISININ-STEROID CONJUGATE AND PREPARATION METHOD AND APPLICATION THEREOF

(71) Applicant: YUNBAIYAO ZHENGWU SCIENCE AND TECHNOLOGY (SHANGHAI) CO., LTD., Shanghai (CN)

(72) Inventors: Jinghua Zhang, Shanghai (CN); Zhengwu Shen, Shanghai (CN)

(73) Assignee: YUNBAIYAO ZHENGWU SCIENCE AND TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/657,908

(22) Filed: Oct. 18, 2019

(65) Prior Publication Data

US 2020/0046679 A1    Feb. 13, 2020

Related U.S. Application Data (63) Continuation of application No. PCT/CN2018/082120, filed on Apr. 8, 2018.

(30) Foreign Application Priority Data

Apr. 28, 2017  (CN) .......................... 2017 1 0294320

(51) Int. Cl.
   *A61K 31/357*   (2006.01)
   *A61K 47/28*    (2006.01)
   *A61P 35/00*    (2006.01)

(52) U.S. Cl.
   CPC ............ *A61K 31/357* (2013.01); *A61K 47/28* (2013.01); *A61P 35/00* (2018.01)

(58) Field of Classification Search
   CPC ....... A61K 35/00; A61K 47/28; A61K 321/35
   See application file for complete search history.

(56) References Cited

PUBLICATIONS

Antonios S. Letis et al., Synthesis and cytotoxic activity of new artemisinin hybrid molecules against human leukemia cells, Bioorganic & Medicinal Chemistry, vol. 25, Issue 13, 2017, pp. 3357-3367, ISSN 0968-0896.

*Primary Examiner* — Marcos L Sznaidman
*Assistant Examiner* — Rayna Rodriguez (57) ABSTRACT

Described is a dihydroartemisinin-steroid conjugate of formula (I), or a pharmaceutically acceptable salt thereof, where position 10 of dihydroartemisinin is linked to the steroid through a linker X. This application further provides a preparation method of the dihydroartemisinin-steroid conjugate and an application of the dihydroartemisinin-steroid conjugate in the preparation of a drug for treating cancer. The dihydroartemisinin-steroid conjugate of the invention exhibits potent inhibitory activity against various tumor cells and low cytotoxicity, moreover, the conjugate is capable of penetrating the blood-brain barrier, having a broad application prospect.

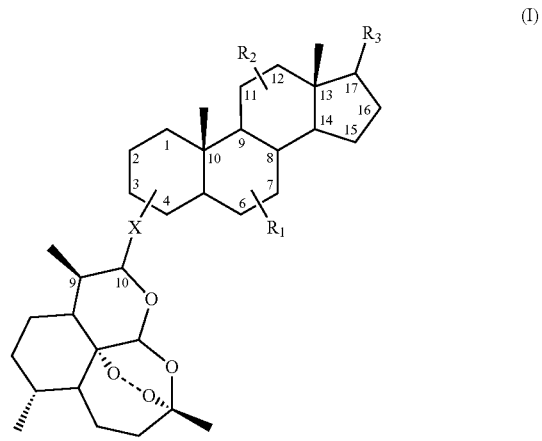

3 Claims, 1 Drawing Sheet

DIHYDROARTEMISININ-STEROID CONJUGATE AND PREPARATION METHOD AND APPLICATION THEREOF

CROSS-REFERENCE TO RELATED APPLICATIONS

This application is a continuation application of International Patent Application PCT/CN2018/082120, filed on Apr. 8, 2018, which claims the benefit of priority from Chinese Patent Application No. 201710294320.6, filed on Apr. 28, 2017. The content of the aforementioned application, including any intervening amendments thereto, is incorporated herein by reference.

BACKGROUND OF THE PRESENT INVENTION

Field of Invention

The present invention relates to pharmacochemistry, and more particularly to a dihydroartemisinin-steroid conjugate and a preparation method and an application thereof.

Description of Related Arts

Since artemisinin has been found to have a strong antimalarial effect in the 1970s, artemisinin, artesunate, artemether, dihydroartemisinin and combinations thereof have been approved as antimalarial drugs in China and also widely used around the world. At the same time, such compounds have also been widely reported to have anticancer effects. Among them, dihydroartemisinin shows more significant anticancer activity. In recent years, various artemisinin derivatives, including dihydroartemisinin and its dimers, artesunate and artemether, have been intensively studied with respect to their anticancer activities. It has been found in in-vitro experiments that these compounds are effective not only for leukemia and colon cancer, but also for other cancers such as melanoma, breast cancer, ovarian cancer, prostate cancer and kidney cancer.

Lung cancer has the fastest growth in morbidity and mortality, which is one of the malignant tumors with the greatest threat to human health and life. Lung cancer is divided into two categories: small cell lung cancer and non-small cell lung cancer. Small cell lung cancer is mainly characterized by neuroendocrine characteristics with high degree of malignancy, rapid growth, early lymphatic metastasis and hematogenous dissemination and high sensitivity to chemotherapy and radiotherapy. Non-small cell lung cancer accounts for 80%-85% of all lung cancer cases, and most of the non-small cell lung cancer lacks neuroendocrine characteristics, and is not very sensitive to the chemotherapy and radiotherapy. However, chemotherapy is still the main method for the treatment of non-small cell lung cancer, although it can only prolong patient survival and improve quality of life. Therefore, the development of new low-toxic broad-spectrum tumor drugs is still a major challenge for the treatment of non-small cell lung cancer and drug-resistant non-small cell lung cancer.

SUMMARY OF THE PRESENT INVENTION

An object of the present invention is to provide a dihydroartemisinin-steroid conjugate, which has potent anticancer activities, and thus is suitable for the treatment of non-small cell lung cancer, brain cancer and other malignant tumors.

The technical solutions of the invention are described as follows.

Firstly, the present invention provides a dihydroartemisinin-steroid conjugate of formula (I), or an isomer, a pharmaceutically-acceptable salt or a prodrug thereof (I)

wherein dihydroartemisinin at position 10 is linked by a linker X with a steroid nucleus;

the linker X is an atom or a group for linking two molecules, and is selected from $CH_2$, O, S, N, —$CO_2$—, $SO_2$—, a $C_2$-$C_{10}$ diol and triol, a benzenediol derivative, a benzenetriol derivative, an aminophenol derivative, an aminobenzoic acid derivative, a hydroxybenzoic acid derivative, a poly-substituted benzene ring and heterocyclic ring containing two or more carboxylic groups, a $C_2$-$C_{10}$ dicarboxylic and poly-carboxylic acid, a $C_2$-$C_{10}$ dithiol compound, a $C_2$-$C_{10}$ diamine, a $C_2$-$C_{10}$ hydroxy acid, a $C_3$-$C_{10}$ amino acid and a $C_3$-$C_{10}$ amino alcohol;

$R_1$ is selected from H, OH, $NH_2$, SH, a halogen, a $C_1$-$C_{10}$ alkoxyl group, a $C_2$-$C_{10}$ haloalkoxyl group, a $C_2$-$C_{10}$ alkoxy alcohol or alkoxy polyol, or a sulfonate or a salt thereof of a $C_2$-$C_{10}$ alkoxy alcohol or alkoxy polyol, a $C_2$-$C_{10}$ alkoxy ether, a $C_2$-$C_{10}$ alkoxycarboxyl acid or alkoxy polycarboxylic acid or salts thereof, a $C_1$-$C_{10}$ alkoxysulfonic acid or salts thereof, a $C_1$-$C_{10}$ alkoxyamine, a $C_1$-$C_{10}$ alkoxy amide, a $C_2$-$C_{10}$ oxyl olefin, a $C_2$-$C_{10}$ oxyl alkyne, a $C_3$-$C_8$ cycloalkyloxyl group, a $C_1$-$C_{10}$ alkoxyimine, a hydroxylamine, a hydroxylamine sulfonate or salts thereof, a sulfinate, an amide group, a substituted or unsubstituted phenoxyl group, a substituted or unsubstituted benzyloxyl group, a substituted or unsubstituted naphthyloxyl group, a $C_1$-$C_{10}$ dialkylamino group such as dimethylamino group and diethylamino group, five- to eight-membered ring having 1-4 heteroatoms such as piperazine, piperidine, pyrrole and tetrahydropyrrole, or a $C_3$-$C_6$ monosaccharide such as fructose, galactose, ribose and deoxyribose, wherein the monosaccharide is linked to the steroid nucleus through a glycosidic bond;

$R_2$ is selected from H, OH, $NH_2$, SH, a halogen, a sulfonate or a salt thereof, a sulfinate or a salt thereof, an amide group, a $C_1$-$C_{10}$ alkoxyl group, a $C_2$-$C_{10}$ haloalkoxyl group, a $C_2$-$C_{10}$ alkoxy alcohol or alkoxy polyol, a sulfonate or a salt thereof of a $C_2$-$C_{10}$ alkoxy alcohol or alkoxy polyol, sulphate of alkoxy alcohol or alkoxy polyol having 1 to 10 carbon atoms, a $C_1$-$C_{10}$ alkoxy ether, a $C_1$-$C_{10}$ alkoxycarboxyl acid or alkoxy polycarboxylic acid or a salt thereof, a $C_1$-$C_{10}$ alkoxysulfonic acid or a salt thereof, a $C_1$-$C_{10}$ alkoxyamine, a $C_1$-$C_{10}$ alkoxy amide, a $C_2$-$C_{10}$ oxyl olefin, a $C_2$-$C_{10}$ oxyl alkyne, a $C_3$-$C_8$ cycloalkyloxyl group, a $C_1$-$C_{10}$ alkoxyimine, hydroxylamine, hydroxylamine sulfonate or a salt thereof, a substituted or unsubstituted phenoxyl group, a substituted or unsubstituted benzyloxyl group, a substituted or unsubstituted naphthyloxyl group, a $C_1$-$C_{10}$ dialkylamino group such as dimethylamino group and diethylamino group, a five- to eight-membered ring having 1-4 heteroatoms such as piperazine, piperidine, pyrrole and tetrahydropyrrole, or a $C_3$-$C_6$ monosaccharide, wherein the monosaccharide is linked to the steroid nucleus through a glycosidic bond;

$R_3$ is selected from H, OH, $NH_2$, SH, a halogen, a sulfonate or a salt thereof, a sulfinate or a salt thereof, an amide group, a $C_1$-$C_{10}$ alkyl group, a $C_2$-$C_{10}$ haloalkyl group, a $C_1$-$C_{10}$ alcohol or polyol, a sulfonate or a salt thereof of a $C_1$-$C_{10}$ alcohol or polyol, sulphate of alkoxy alcohol or alkoxy polyol having 1 to 10 carbon atoms, a $C_2$-$C_{10}$ ether or a $C_2$-$C_{10}$ monoether of a polyol, a $C_1$-$C_{10}$ carboxylic acid or polycarboxylic acid or a salt thereof, a $C_1$-$C_{10}$ alkylsulfonic acid or a salt thereof, a $C_1$-$C_{10}$ amine, a $C_1$-$C_{10}$ amide, a $C_2$-$C_{10}$ alkene, a $C_2$-$C_{10}$ alkyne, a $C_3$-$C_8$ cycloalkane, a $C_1$-$C_{10}$ ketone, a $C_1$-$C_{10}$ alkylimine, a $C_1$-$C_{10}$ alkoxyimine, a hydroxyimine, a hydroxylamine sulfonate or a salt thereof, a $C_1$-$C_{10}$ alkylsulfonate or a salt thereof, a $C_1$-$C_{10}$ alkyl sulfinate, a $C_1$-$C_{10}$ alkylamide, a substituted or unsubstituted phenyl or phenoxyl group, a substituted or unsubstituted benzyl group, a substituted or unsubstituted naphthyl group, a $C_1$-$C_{10}$ dialkylamino group such as dimethylamino group and diethylamino group, a five- to eight-membered ring having 1-4 heteroatoms such as piperazine, piperidine, pyrrole and tetrahydropyrrole, a $C_3$-$C_6$ monosaccharide having 3-6 carbons, C-17 side chain of cholic acid or a derivative thereof, C-17 side chain of a phytosterol such as ergosterol and soybean sterol or a derivative thereof, C-17 side chain of a steroid hormone such as estrone, estradiol, estriol, hydrocortisone, cortisone, dexamethasone, prednisone, prednison and aldosterone, a side chain forming a spiro with 16-hydroxyl group, such as diosgenin, hecogenin, sisalagenin, tigogenin and yamogenin or C-17 side chain of a steroidal alkaloid such as solanine, β-citronine, solanocapsine, zygadenine, veratramine, jerveramine, peimine and cyclopamine; wherein the monosaccharide is linked to the steroid nucleus through a glycosidic bond and $R_3$ is α-configuration or β-configuration;

In the formula (I), ⋯⋯ represents α-substitution and ▬ represents β-substitution.

In an embodiment, the linker X comprises O, S, N, —$CH_2$—, —NR—, —BH—, —BR—, —P(O)—, —NH—NH—, —$OSO_2$—, —O—CO—O—, —OCO—$(CH_2)_n$—COO—, —$O(CH_2)_nO$—, —$O(CH_2OCH_2)_nO$—, —O—$SO_2$—O—, —O—$PO_2$—O—, —O—BO—O—, —$(CH_2)_n$—O—, —O-Ph-O—, —$O(CH_2)_nNR(CH_2)_mO$—, —$OOC(CH_2)_nNR(CH_2)_m$—COO—, —$O(CH_2)_2N(CH_2)_2N(CH_2)_2O$—, —OPh(Y)—O—, —O-Ph(Y)—COO—, —OOC—$(CH_2)_n$Ph(Y)$(CH_2)_m$COO—, —OOCPh(Y)COO—, —$OCH_2CH_2NHPh(Y)NHCH_2CH_2O$— and a five- or six-membered heterocyclic ring having 1-4 heteroatoms and derivatives thereof such as furan, pyrimidine, thiazole, thiophene, oxazole and indole;

wherein R is H or a $C_1$-$C_{10}$ saturated or unsaturated hydrocarbon; Y is OR', NHR', NR'$_2$, a halogen, —$CF_3$, —COOH, —COOR', —$CONH_2$, —CONR'$_2$, —CN, —$NO_2$, —$SO_3$ or —$SO_2R'$, Y may substitute H at different positions of the benzene ring; R' is H or a $C_1$-$C_{10}$ saturated or unsaturated hydrocarbyl group; and n and m are respectively 0-10.

In an embodiment, the linker X is O, —$CH_2O$— or —O—$CH_2CH_2$—O—.

One end of the linker X is linked to the dihydroartemisinin at position 10, and the other end is linked to the steroid nucleus at position 2, 3, 5, 6, 7, 11, 12, 15, 16 or 17, or linked to a side chain of the steroid. X is preferably linked to the steroid at position 3, 6 or 7. The linker X is spatially α-configuration or β-configuration.

In the formula (I) of the present invention, $R_1$ may be located at position 2, 3, 4, 6 or 7 of the steroid nucleus. $R_1$ may also be a double bond located at position 4, 5 or 6. $R_1$ is preferably OH, $NH_2$, $OSO_3H$ or dialkylamine group such as dimethylamine group. $R_1$ is preferably located at position 5, 6 or 7, and is spatially α-configuration or β-configuration.

$R_2$ can be located at position 11, 12, 15 or 16 of the steroid nucleus. $R_2$ is preferably OH, $NH_2$, $OSO_3H$ or a dialkylamine group such as dimethylamine group. $R_2$ is preferably located at position 12 or 16, and is spatially α-configuration or β-configuration.

In the invention, the steroidal nucleus refers to all structures having cyclopentano-perhydrophenanthrene moiety, and comprises natural and synthetic steroids and derivatives thereof, which further comprises sterane, androstane, estradiol, pregnane, cholane, ergosterol, stigmasteroid and isosteroid. Specifically, the steroidal nucleus comprises cholic acid (comprising natural or synthetic amino acid derivatives such as taurocholic acid and glycocholic acid), deoxycholic acid (comprising natural or synthetic amino acid derivatives such as taurodeoxycholic acid and glycodeoxycholic acid), hyodeoxycholic acid (comprising natural or synthetic amino acid derivatives such as taurohyodeoxycholic acid and glycohyodeoxycholic acid), ursodeoxycholic acid (comprising natural or synthetic derivatives such as tauroursodeoxycholic acid and glycoursodeoxycholic acid), chenodeoxycholic acid (comprising natural or synthetic derivatives such as taurochenodeoxycholic acid and glycodeoxycholic acid), Obeticholic acid and analogues and derivatives thereof, cholesteryl, ergosterol, soybean sterol, phytosterols such as 5α and 5β sitosterol, steroid hormones and derivatives thereof such as estrone, estradiol, and estriol and derivatives thereof, glucocorticoids and derivatives thereof such as hydrocortisone, cortisone, dexamethasone, prednisone and prednison and derivatives thereof; mineralocorticoids and derivatives thereof such as aldosterone, steroidal saponins such as dioscin, heconin, sisalanin, tigonin and collettinside and other plant saponins and sapogenins thereof such as diosgenin, hecogenin, sisalagenin, tigogenin and yamogenin, steroid alkaloids such as solanine, β-citronine, solanocapsine, zygadenine, veratramine, jerveramine, peimine and cyclopamine, and derivatives of the above steroids.

The conjugate of formula (I) of the present invention comprises all isomers thereof such as positional isomers and stereoisomers.

In an embodiment, the conjugate of formula (I) is selected from:

-continued

In some embodiments, the conjugate of formula (I), may be:

JZ-01

JZ-02

JZ-03 and

JZ-04

JZ-05

JZ-06

JZ-07

JZ-08

JZ-09

JZ-10

JZ-11

JZ-12

According to the present invention, the pharmaceutically-acceptable salt of the dihydroartemisinin-steroid conjugate is selected from a potassium salt, a sodium salt, a calcium salt, a magnesium salt, and an organic salt formed with natural and non-natural organic nitrogen-containing compounds.

Secondly, the present invention provides a pharmaceutical composition comprising one or more of the above-described dihydroartemisinin-steroid conjugates, or isomers, pharmaceutically acceptable salts or prodrugs thereof, and a pharmaceutically-acceptable carrier.

The pharmaceutically-acceptable carrier that is non-toxic is helpful for the administration to subjects without adversely affecting the therapeutic effect of the conjugates. Such carrier may be any solid, liquid or semi-solid excipient or a gaseous excipient in an aerosol composition which is generally available to those skilled in the art. The solid pharmaceutical excipients may be starch, cellulose, talc, glucose, lactose, sucrose, gelatin, malt, rice, flour, chalk, silica gel, magnesium stearate, sodium stearate, stearyl glyceryl ester, sodium chloride or anhydrous skim milk. The liquid and semi-solid excipients may be selected from glycerin, propylene glycol, water, ethanol and various oils, for example, those derived from petroleum, animal and vegetable such as p soybean oil, mineral oil and sesame oil, and synthetic oils, wherein a liquid carrier is preferred, and more preferably an injectable solution comprising water, saline, aqueous glucose and glycol. Moreover, other adjuvants such as flavoring agents and sweeteners may also be introduced into the composition. The pharmaceutical composition of the present invention can be administered orally or by other means such as injection, transdermal administration, spray administration, rectal administration and vaginal administration. Oral administration is preferred since it can be adjusted according to the extent of the disease.

The pharmaceutical composition of the invention can be combined with other anticancer drugs, comprising doxorubicin, bleomycin, vinblastine, paclitaxel, etoposide, 5-FU, cyclophosphamide, methotrexate, cisplatin, retinoic acid, temozolomide, actinomycin, imatinib, gefitinib, sorafenib, erlotinib, sunitinib, rituximab, cetuximab and herceptin, PD-1 inhibitors such as nivolumab and pembrolizumab and PD-L1 inhibitors such as atezolizumab, durvalumab and avelumab.

The pharmaceutical composition of the present invention can be administered in combination with a biosynthetic precursor of heme such as 5-aminolevulinic acid (ALA) and its homologues.

The pharmaceutical composition of the present invention can also be used in combination with an amino acid such as δ-aminolevulinic acid to treat cancer.

The pharmaceutical composition of the present invention can also be used in combination with other treatment methods such as surgery, radiation therapy, immunotherapy and bone marrow transplantation.

The pharmaceutical compositions of the present invention can be prepared into various dosage forms according to conventional methods in pharmaceuticals. For example, the composition can be mixed with one or more carriers and then formulated into a desired dosage form such as a tablet, pill, capsule, semisolid, a powder, a slow-release form, solution, suspension, a formulation, aerosol, etc.

Thirdly, the invention provides a method of preparing the above-described dihydroartemisinin-steroid conjugate, comprising:

linking dihydroartemisinin at position 10 with a hydroxyl group of steroid at position 2, 3, 5, 6, 7, 11, 12, 15, 16 or 17 through the formation of an ether bond to obtain a dihydroartemisinin-steroid conjugate.

The method is specifically described as follows.

Route 1

Dihydroartemisinin is directly linked with the hydroxyl group of the steroid compound at position 2, 3, 5, 6, 7, 11, 12, 16 or 17 in the presence of a Lewis acid to form an ether bond so as to obtain the dihydroartemisinin-steroid conjugate.

Route 2

In the case that there are a plurality of hydroxyl groups on the steroid compound, especially a hydroxyl group with less steric hindrance, for example, in the case of the presence of a 3-position hydroxyl group and a hydroxyl group at another position, in order to allow the dihydroartemisinin to link to a specific position of the steroid, it is required to first protect the 3-position hydroxyl group with less steric hindrance using a protecting group such as acetyl, benzoyl, Piv, chloroacetyl, benzyl, MOM, TMS, TES, TMBS, TIP and TBDPS, and then the steroid carrying the protecting group is reacted with the dihydroartemisinin in the presence of Lewis acid, such that the dihydroartemisinin is linked by an ether bond to the hydroxyl group at the specific position of the steroid. Finally, the protecting group is removed under acidic, basic or neutral conditions to obtain the dihydroartemisinin-steroid conjugat.

Fourthly, the present invention provides another method for preparing the above-described dihydroartemisinin-steroid conjugate, comprising:

linking dihydroartemisinin or a derivative thereof with a linker X via an ester bond, an ether bond, an amide bond, a carbon-carbon single bond, a carbon-nitrogen single bond or a carbon-sulfur single bond to form an intermediate, and linking the intermediate by a covalent bond with the steroid at position 2, 3, 5, 6, 7, 11, 12, 15, 16 or 17 to form the dihydroartemisinin-steroid conjugate;

wherein the linker X generally comprises two to three reactive groups which can be bonded, and is selected from a halogenated alcohol, a halogenated acid, an amino acid, a hydroxy acid, an amino alcohol, a polyhydric alcohol such as propylene glycol and glycerin, a polybasic acid such as oxalic acid, malonic acid and EDTA, a saccharide such as fructose, ribose, erythrose and erythritol, a polyamine such as ethylenediamine, propylenediamine, butanediamine, phenylenediamine and piperazine, a polyphenol such as resorcinol, phloroglucinol and derivatives thereof, a heterocyclic compound such as piperazine and aminothiazole acetic acid derivatives. Preferably, the linker X is a polyhydric alcohol or a halogenated alcohol such as bromoethanol, ethylene glycol and glycerol and the like, or a polyphenol derivative such as resorcinol, phloroglucinol and dihydroxybenzoic acid.

The method is specifically described as follows.

Route 1

The dihydroartemisinin and the linker such as a polyol or a halogenated alcohol (such as bromoethanol, ethylene glycol, glycerol, resorcinol and phloroglucin) are reacted in the presence of a Lewis acid to form an intermediate Z with a hydroxyl group, a phenolic hydroxyl group or a bromine atom; and then the intermediate Z is reacted with the hydroxyl group at position 2, 3, 5, 6, 7, 11, 12, 15, 16 or 17 of the steroid in the presence of a Lewis acid or a base to form an ether, as shown in the following scheme:

Intermediate Z

Route 2

In the case that there are more than one hydroxyl group on the steroid, particularly a less sterically-hindered hydroxy group such as 3-OH and a hydroxyl group at another position, in order to allow the dihydroartemisinin to link the steroid at a specific position through the linker, it is necessary to first use a protecting group such as acetyl, benzoyl, Piv, chloroacetyl, benzyl, MOM, TMS, TES, TMBS, TIP and TBDPS to protect the less sterically-hindered hydroxyl group, and then the steroid carrying the protecting group is reacted with the intermediate Z in the presence of a Lewis acid, such that the dihydroartemisinin is linked by an ether bond to the specific position of the steroid. Finally, the protecting group is removed under acidic, basic or neutral conditions to obtain the dihydroartemisinin-steroid conjugate.

In the above reaction, the acid used in the acidic condition may be a protic acid or a Lewis acid, preferably boron trifluoride etherate, p-toluenesulfonic acid, trifluoroacetic acid, sulfuric acid or hydrochloric acid. The base used in the basic condition may be an organic base or an inorganic base, preferably triethylamine, pyrrolidine, sodium carbonate or sodium bicarbonate. The solvent used in each reaction may be a protic solvent or an aprotic solvent, preferably diethyl ether, tetrahydrofuran, acetonitrile, DMF, DMSO, alcohol or water. The reaction temperature is generally 10-80° C.

The crude product of the above reaction can be further purified by chromatography, generally by column chromatography, wherein silica gel or aluminum oxide is used as a filler, and the eluent may be a mixture of petroleum ether and acetone or a mixture of petroleum ether and ethyl acetate in various ratios.

Fifthly, the invention provides an application of the above-described dihydroartemisinin-steroid conjugate or an isomer, a pharmaceutically acceptable salt or a prodrug thereof in the preparation of a drug for treating cancer.

The cancer comprises brain cancer, glioma, endometrial cancer, ovarian cancer, cervical cancer, breast cancer, colon cancer, lung cancer, prostate cancer, liver cancer, leukemia, lymphoma, skin cancer, basal cell tumor, hemangioma, uterine cancer, laryngeal cancer, stomach cancer, lip cancer, esophageal cancer, nasopharyngeal cancer, gallbladder cancer, pancreatic cancer, kidney cancer, tongue cancer, bladder cancer, melanoma, lipoma, thyroid cancer, thymic cancer and bone cancer, where the lung cancer comprises non-small cell lung cancer and EGFR-TKI drug-resistant non-small cell lung cancer.

The dihydroartemisinin-steroid conjugate of the invention can be easily prepared and has good chemical stability and low toxicity. Moreover, the conjugate also exhibits potent inhibitory activity against various tumor cells in an in-vitro test, especially for the highly-malignant medulloblastoma cells and EGFR-TKI drug-resistant non-small cell lung cancer cells. The dihydroartemisinin-steroid conjugate provided herein has a potent inhibitory activity against tumor cells and low toxicity, thus it has broad application prospects in the treatment of cancers.

BRIEF DESCRIPTION OF THE DRAWINGS

The invention will be further illustrated with reference to the accompanying drawings and embodiments.

DETAILED DESCRIPTION OF THE EMBODIMENTS

Example 1

Synthesis of JZ-01

To a solution of dihydroartemisinin (569 mg, 2.0 mmol) and cholic acid (817 mg, 2.0 mmol) in diethyl ether (50 mL) was slowly dropwise added $BF_3.Et_2O$ (1 mL) at −78° C. The temperature was naturally raised to ambient temperate and then the reaction mixture was stirred overnight. When the reaction was determined by TLC to be completed, a saturated aqueous $NaHCO_3$ solution (30 mL) was slowly added to quench the reaction, and then the reaction mixture was extracted with ethyl acetate (30 mL×3). The organic phases were combined, washed with water (50 mL) and saturated NaCl solution (50 mL), dried with anhydrous $MgSO_4$ and filtered. The filtrate was rotatorily evaporated under vacuum to obtain a crude product, which was purified by silica gel column chromatography to give a colorless oily compound JZ-01 (726 mg, yield 53.8%), where an eluent was a mixture of petroleum ether and ethyl acetate in a ratio of 3:1-1:1.

$^1$H NMR (400 MHz, $CDCl_3$): δ 5.47 (s, 1H), 4.93 (d, J=3.3 Hz, 1H), 4.00 (s, 1H), 3.88 (s, 1H), 3.51 (t, J=11.0 Hz, 1H), 2.64-2.56 (m, 1H), 2.47-2.21 (m, 4H), 2.10-2.02 (m, 2H), 1.99-1.85 (m, 5H), 1.72 (m, 8H), 1.53 (m, 5H), 1.45 (m, 6H), 1.40-1.30 (m, 5H), 1.31-1.23 (m, 4H), 1.16 (m, 2H), 0.99 (m, 7H), 0.89 (m, 8H), 0.71 (s, 3H).

$^{13}$C NMR (100 MHz, $CDCl_3$): δ 104.03, 100.14, 88.08, 81.29, 68.67, 52.65, 46.86, 46.51, 44.56, 42.21, 41.33, 39.32, 37.47, 36.51, 35.58, 35.29, 35.22, 34.87, 34.73, 31.53, 30.84, 30.68, 30.54, 30.31, 30.18, 30.35, 30.25, 29.72, 28.71, 27.58, 26.70, 26.30, 24.70, 23.22, 22.60, 20.41, 17.24, 13.08, 12.46.

Example 2

Synthesis of JZ-02

To a solution of dihydroartemisinin (569 mg, 2.0 mmol) and ursodeoxycholic acid (785 mg, 2.0 mmol) in diethyl ether (50 mL) was slowly dropwise added $BF_3.Et_2O$ (1 mL) at −78° C. The temperature was naturally raised to ambient temperate and then the reaction mixture was stirred overnight. When the reaction was determined by TLC to be completed, a saturated aqueous $NaHCO_3$ solution (30 mL) was slowly added to quench the reaction, and the reaction mixture was extracted with ethyl acetate (30 mL×3). The organic phases were combined, washed with water (50 mL) and saturated NaCl solution (50 mL), dried with anhydrous $MgSO_4$ and filtered. The filtrate was rotatorily evaporated under vacuum to give a crude product, which was purified by silica gel column chromatography to give a colorless oily compound JZ-02 (748 mg, yield 56.8%), where an eluent was a mixture of petroleum ether and ethyl acetate in a ratio of 4:1-2:1.

$^1$H NMR (400 MHz, $CDCl_3$): δ 5.46 (s, 1H), 4.92 (d, J=3.3 Hz, 1H), 3.61 (m, 2H), 2.67-2.55 (m, 1H), 2.47-2.34 (m, 2H), 2.28 (ddd, J=15.8, 9.6, 6.5 Hz, 1H), 2.04 (m, 2H), 1.94-1.71 (m, 9H), 1.71-1.55 (m, 4H), 1.54-1.41 (m, 11H), 1.40-1.21 (m, 9H), 1.19-1.01 (m, 3H), 0.98-0.89 (m, 12H), 0.70 (s, 3H).

$^{13}$C NMR (100 MHz, $CDCl_3$): δ 178.71, 104.07, 100.21, 88.08, 81.22, 71.41, 55.61, 54.92, 52.61, 44.51, 43.79, 42.37, 40.07, 39.19, 37.49, 36.99, 36.48, 35.21, 35.01, 34.71, 34.25, 33.60, 30.84, 30.82, 30.75, 28.85, 28.63, 26.90, 26.27, 24.70, 20.56, 23.53, 21.24, 20.41, 18.42, 13.16, 12.15.

Example 3

Synthesis of JZ-03

To a solution of dihydroartemisinin (569 mg, 2.0 mmol) and hyodeoxycholic acid (785 mg, 2.0 mmol) in diethyl ether (50 mL) was slowly dropwise added $BF_3.Et_2O$ (1 mL) at −78° C. The temperature was naturally raised to ambient temperate and the reaction mixture was stirred overnight. When the reaction was determined to be completed by TLC, a saturated aqueous $NaHCO_3$ solution (30 mL) was slowly added to quench the reaction, and the reaction mixture was then extracted with ethyl acetate (30 mL×3). The organic phases were combined, washed with water (50 mL) and saturated NaCl solution (50 mL), dried with anhydrous $MgSO_4$ and filtered. The filtrate was rotatorily evaporated under vacuum to give a crude product, which was purified by silica gel column chromatography to give a colorless oily compound JZ-03 (653 mg, yield 49.5%), where an eluent was a mixture of petroleum ether and ethyl acetate in a ratio of 8:1-1:1.

$^1$H NMR (400 MHz, $CDCl_3$): δ 5.41 (s, 1H), 4.96 (d, J=3.5 Hz, 1H), 4.14-4.02 (m, 1H), 3.64 (dt, J=15.5, 5.5 Hz,

1H), 2.68-2.58 (m, 1H), 2.35 (m, 3H), 2.12-1.95 (m, 2H), 1.95-1.56 (m, 12H), 1.56-1.21 (m, 16H), 1.12 (m, 6H), 1.02-0.89 (m, 10H), 0.86 (d, J=7.3 Hz, 3H), 0.65 (s, 3H).

$^{13}$C NMR (100 MHz, CDCl$_3$): δ 179.13, 104.09, 98.78, 88.20, 81.19, 72.49, 71.73, 56.21, 55.93, 52.64, 47.88, 44.45, 42.88, 39.99, 37.55, 36.51, 36.00, 35.43, 35.34, 34.69, 34.51, 31.64, 30.24, 30.36, 30.44, 30.75, 30.77, 30.87, 29.67, 28.11, 26.26, 24.64, 24.22, 23.77, 20.75, 20.41, 18.25, 13.16, 12.02.

Example 4

Synthesis of JZ-04

To a solution of dihydroartemisinin (569 mg, 2.0 mmol) and chenodeoxycholic acid (785 mg, 2.0 mmol) in diethyl ether (50 mL) was slowly dropwise added BF$_3$·Et$_2$O (1 mL) at −78° C. The temperature was naturally raised to ambient temperate and the reaction mixture was stirred overnight. When the reaction was determined to be completed by TLC, a saturated aqueous NaHCO$_3$ solution (30 mL) was slowly added to quench the reaction, and the reaction mixture was extracted with ethyl acetate (30 mL×3). The organic phases were combined, washed with water (50 mL) and saturated NaCl solution (50 mL), dried with anhydrous MgSO$_4$ and filtered. The filtrate was rotatorily evaporated under vacuum to give a crude product, which was purified by silica gel column chromatography to give a colorless oily compound JZ-04 (723 mg, yield 54.8%), where an eluent was a mixture of petroleum ether and ethyl acetate in a ratio of 10:1-1:1 $^1$H NMR (400 MHz, CDCl$_3$): δ 5.46 (s, 1H), 4.93 (d, J=3.1 Hz, 1H), 3.88 (s, 1H), 3.48 (t, J=10.8 Hz, 1H), 2.65-2.55 (m, 1H), 2.46-2.33 (m, 2H), 2.27 (m, 1H), 1.87 (m, 16H), 1.52-1.13 (m, 21H), 0.95 (m, 14H), 0.66 (s, 3H).

$^{13}$C NMR (100 MHz, CDCl$_3$): δ 179.74, 104.02, 100.40, 88.09, 81.30, 77.49, 68.70, 55.79, 52.63, 50.53, 44.59, 42.73, 41.33, 39.56, 39.33, 37.47, 36.51, 35.86, 35.39, 35.37, 35.23, 34.89, 34.72, 32.88, 30.94, 30.92, 30.79, 29.12, 28.18, 26.29, 24.70, 24.57, 23.70, 22.90, 20.64, 20.41, 18.27, 13.20, 11.78.

Example 5

Synthesis of JZ-05

To a solution of dihydroartemisinin (569 mg, 2.0 mmol) and diosgenin (829 mg, 2.0 mmol) in diethyl ether (50 mL) was slowly dropwise added BF$_3$·Et$_2$O (1 mL) at −78° C. The temperature was naturally raised to ambient temperate and the reaction mixture was stirred overnight. When the reaction was determined by TLC to be completed, a saturated aqueous NaHCO$_3$ solution (30 mL) was slowly added to quench the reaction, and the reaction mixture was extracted with ethyl acetate (30 mL×3). The organic phases were combined, washed with water (50 mL) and saturated NaCl solution (50 mL), dried with anhydrous MgSO$_4$ and filtered. The filtrate was rotatorily evaporated under vacuum to give a crude product, which was purified by silica gel column chromatography to give a white solid compound JZ-05 (975 mg, yield 71.6%), where an eluent was a mixture of petroleum ether and ethyl acetate in a ratio of 40:1-15:1.

$^1$H NMR (400 MHz, CDCl$_3$): δ 5.48 (s, 1H), 5.36 (d, J=4.9 Hz, 1H), 4.94 (d, J=3.4 Hz, 1H), 4.43 (dd, J=15.0, 7.5 Hz, 1H), 3.60 (dt, J=9.6, 4.7 Hz, 1H), 3.50 (dd, J=10.3, 3.5 Hz, 1H), 3.40 (t, J=10.9 Hz, 1H), 2.67-2.57 (m, 1H), 2.44-2.26 (m, 3H), 2.02 (m, 3H), 1.93-1.80 (m, 5H), 1.78-1.72 (m, 2H), 1.71-1.57 (m, 7H), 1.56-1.44 (m, 8H), 1.40-1.09 (m, 7H), 1.06-0.93 (m, 11H), 0.90 (d, J=7.3 Hz, 3H), 0.81 (m, 6H).

$^{13}$C NMR (100 MHz, CDCl$_3$): δ 140.74, 121.39, 109.32, 104.05, 99.45, 88.09, 81.27, 80.87, 76.13, 66.87, 62.05, 56.46, 52.62, 50.01, 44.52, 41.61, 40.27, 39.78, 37.47, 36.94, 36.86, 36.49, 34.71, 32.07, 31.87, 31.42, 31.39, 30.76, 30.32, 28.81, 27.59, 26.28, 24.70, 24.52, 20.87, 20.42, 19.52, 17.18, 16.32, 14.57, 13.12.

Example 6

Synthesis of JZ-06

To a solution of dihydroartemisinin (569 mg, 2.0 mmol) and ergosterol (793 mg, 2.0 mmol) in diethyl ether (50 mL) was slowly dropwise added BF$_3$.Et$_2$O (1 mL) at −78° C. The temperature was naturally raised to ambient temperate and the reaction mixture was stirred overnight. When the reaction was determined by TLC to be completed, a saturated aqueous NaHCO$_3$ solution (30 mL) was slowly added to quench the reaction, and the reaction mixture was extracted with ethyl acetate (30 mL×3). The organic phases were combined, washed with water (50 mL) and saturated NaCl solution (50 mL), dried with anhydrous MgSO$_4$ and filtered. The filtrate was rotatorily evaporated under vacuum to give a crude product, which was purified by silica gel column chromatography to give a white solid compound (895 mg, yield 67.5%), where an eluent was a mixture of petroleum ether and ethyl acetate in a ratio of 30:1-15:1.

$^1$H NMR (400 MHz, CDCl$_3$): δ 5.56 (dd, J=5.6, 2.2 Hz, 1H), 5.49 (s, 1H), 5.39 (dt, J=5.3, 2.5 Hz, 1H), 5.33-5.14 (m, 2H), 4.97 (d, J=3.4 Hz, 1H), 3.70 (ddd, J=11.2, 7.8, 4.4 Hz, 1H), 2.69-2.58 (m, 1H), 2.56-2.46 (m, 1H), 2.38 (m, 2H), 2.11-2.01 (m, 3H), 2.00-1.82 (m, 7H), 1.79-1.65 (m, 4H), 1.65-1.56 (m, 2H), 1.53-1.45 (m, 5H), 1.42-1.21 (m, 10H), 1.04 (d, J=6.7 Hz, 3H), 0.89-0.98 (m, 12H), 0.85 (t, J=6.4 Hz, 6H), 0.64 (s, 3H).

$^{13}$C NMR (100 MHz, CDCl$_3$): δ 140.99, 139.97, 135.63, 131.93, 119.47, 116.47, 104.05, 99.60, 88.10, 81.24, 75.07, 55.69, 54.50, 52.63, 46.05, 44.52, 42.81, 40.50, 39.07, 38.81, 37.97, 37.48, 37.26, 36.49, 34.72, 33.10, 30.77, 29.72, 28.35, 27.98, 26.25, 24.52, 24.70, 23.03, 21.13, 21.05, 20.40, 19.98, 19.67, 17.62, 16.21, 13.11, 12.07.

Example 7

Synthesis of JZ-07

JZ-07

To a solution of dihydroartemisinin (569 mg, 2.0 mmol) and lithocholic acid (753 mg, 2.0 mmol) in diethyl ether (50 mL) was slowly dropwise added BF$_3$.Et$_2$O (1 mL) at −78° C. The temperature was naturally raised to ambient temperate and the reaction mixture was stirred overnight. When the reaction was determined by TLC to be completed, a saturated aqueous NaHCO$_3$ solution (30 mL) was slowly added to quench the reaction, and the reaction mixture was extracted with ethyl acetate (30 mL×3). The organic phases were combined, washed with water (50 mL) and saturated NaCl solution (50 mL), dried with anhydrous MgSO$_4$ and filtered. The filtrate was rotatorily evaporated under vacuum to give a crude product, which was purified by silica gel column chromatography to give a colorless oily compound JZ-07 (843 mg, yield 65.5%), where an eluent was a mixture of petroleum ether and ethyl acetate in a ratio of 12:1-2:1.

$^1$H NMR (400 MHz, CDCl$_3$): δ 5.47 (s, 1H), 4.92 (d, J=3.3 Hz, 1H), 3.73-3.53 (m, 1H), 2.66-2.56 (m, 1H), 2.39 (m, 2H), 2.27 (ddd, J=15.8, 9.7, 6.4 Hz, 1H), 2.05 (dt, J=14.5, 3.7 Hz, 1H), 1.99-1.94 (m, 1H), 1.93-1.70 (m, 8H), 1.68-1.55 (m, 3H), 1.51-1.21 (m, 21H), 1.08 (m, 4H), 1.00-0.89 (m, 13H), 0.66 (s, 3H).

$^{13}$C NMR (100 MHz, CDCl$_3$): δ 180.33, 104.04, 100.16, 88.07, 81.26, 76.26, 56.42, 55.98, 52.63, 44.57, 42.77, 41.97, 40.42, 40.12, 37.48, 36.50, 35.85, 35.32, 35.42, 34.74, 32.59, 31.00, 30.85, 30.78, 29.72, 29.01, 28.20, 27.33, 26.40, 26.27, 24.70, 24.57, 24.21, 23.51, 20.89, 20.42, 18.30, 13.18, 12.07.

Example 8

Synthesis of JZ-08

JZ-08

To a solution of dihydroartemisinin (569 mg, 2.0 mmol) and deoxycholic acid (785 mg, 2.0 mmol) in diethyl ether (50 mL) was slowly dropwise added BF$_3$.Et$_2$O (1 mL) at −78° C. The temperature was naturally raised to ambient temperate and the reaction mixture was stirred overnight. When the reaction was determined by TLC to be completed, a saturated aqueous NaHCO$_3$ solution (30 mL) was slowly added to quench the reaction, and then the reaction mixture was extracted with ethyl acetate (30 mL×3). The organic phases were combined, washed with water (50 mL) and saturated NaCl solution (50 mL), dried with anhydrous MgSO$_4$ and filtered. The filtrate was rotatorily evaporated under vacuum to give a crude product, which was purified by silica gel column chromatography to give a colorless oily compound (723 mg, 54.8%), where an eluent was a mixture of petroleum ether and ethyl acetate in a ratio of 12:1-3:1.

$^1$H NMR (400 MHz, CDCl$_3$): δ 5.47 (s, 1H), 4.91 (d, J=3.4 Hz, 1H), 4.02 (s, 1H), 3.67-3.55 (m, 1H), 2.65-2.56 (m, 1H), 2.48-2.25 (m, 3H), 2.07-2.01 (m, 1H), 1.92-1.81 (m, 5H), 1.77-1.70 (m, 3H), 1.68-1.58 (m, 4H), 1.54 (m, 2H), 1.50-1.34 (m, 12H), 1.27 (m, 8H), 1.18-1.06 (m, 2H), 1.01 (d, J=6.2 Hz, 3H), 0.96 (d, J=6.3 Hz, 3H), 0.93-0.85 (m, 7H), 0.71 (s, 3H).

$^{13}$C NMR (100 MHz, CDCl$_3$): δ 179.27, 104.03, 100.49, 88.10, 81.30, 73.32, 52.62, 48.36, 47.33, 46.46, 44.55, 42.00, 37.43, 36.51, 36.06, 35.26, 35.04, 34.66, 34.30, 33.79, 32.64, 30.91, 30.82, 30.68, 29.72, 28.98, 27.43, 27.27, 26.29, 26.06, 24.69, 24.58, 23.62, 23.34, 20.38, 17.33, 13.20, 12.77.

Example 9

Synthesis of 10-(2-bromoethoxy)dihydroartemisinin

To a solution of dihydroartemisinin (284 mg, 1.0 mmol) and 2-bromoethanol (125 mg, 1.0 mmol) in diethyl ether (20 mL) was slowly dropwise added BF$_3$.Et$_2$O (50 μL) at 0° C. After the addition, the reaction mixture was stirred at 0° C.

overnight. When the reaction was determined by TLC to be completed, a saturated aqueous NaHCO$_3$ solution (10 mL) was slowly added to quench the reaction, and then the reaction mixture was extracted with ethyl acetate (10 mL×3). The organic phases were combined, washed with water (20 mL) and saturated NaCl solution (20 mL), dried with anhydrous MgSO$_4$ and filtered. The filtrate was rotatorily evaporated under vacuum to give a crude product, which was purified by silica gel column chromatography to give a white solid compound (203 mg, yield 51.9%), where an eluent was a mixture of petroleum ether and ethyl acetate in a ratio of 30:1-8:1. $^1$H NMR (400 MHz, CDCl$_3$): δ 5.48 (s, 1H), 4.84 (d, J=3.3 Hz, 1H), 4.18-4.07 (m, 1H), 3.81-3.74 (m, 1H), 3.51 (t, J=5.2 Hz, 2H), 2.69-2.59 (m, 1H), 2.40-2.33 (m, 1H), 2.06-1.99 (m, 1H), 1.92-1.84 (m, 2H), 1.76 (m, 1H), 1.68-1.61 (m, 1H), 1.55-1.43 (m, 5H), 1.37-1.21 (m, 3H), 0.95-0.90 (m, 6H).

$^{13}$C NMR (101 MHz, CDCl$_3$): δ 104.10, 102.02, 88.13, 81.08, 77.42, 77.11, 76.79, 68.16, 52.56, 44.35, 37.38, 36.39, 34.66, 31.47, 30.89, 26.16, 24.65, 24.36, 20.39, 13.00.

Example 10

Synthesis of JZ-09

K$_2$CO$_3$ (276 mg, 2.0 mmol) and a catalytic amount of KI were added successively to a solution of 10-(2-bromoethoxy)dihydroartemisinin (391 mg, 1.0 mmol) and ursodeoxycholic acid (392 mg, 1.0 mmol) in DMF (20 mL) at room temperature. The reaction mixture was heated to 70° C. and reacted for 2 h. When the reaction was determined by TLC to be completed, water (20 mL) was slowly added to quench the reaction, and the reaction mixture was extracted with ethyl acetate (20 mL×3). The organic phases were combined, washed with water (30 mL) and saturated NaCl solution (50 mL) in sequence, dried with anhydrous MgSO$_4$ and filtered. The filtrate was rotatorily evaporated under vacuum to give a crude product, which was purified by silica gel column chromatography to give a colorless oily compound (536 mg, yield 76.2%), where an eluent was a mixture of petroleum ether and ethyl acetate in a ratio of 4:1-1:1.

$^1$H NMR (400 MHz, CDCl$_3$): δ 5.45 (s, 1H), 4.84 (d, J=3.4 Hz, 1H), 4.28-4.21 (m, 2H), 4.08-3.98 (m, 1H), 3.68-3.57 (m, 3H), 2.72-2.58 (m, 1H), 2.43-2.34 (m, 2H), 2.28-2.19 (m, 1H), 2.04 (m, 2H), 1.91 (m, 2H), 1.85-1.77 (m, 5H), 1.71-1.60 (m, 5H), 1.53-1.44 (m, 11H), 1.39-1.25 (m, 12H), 1.19-1.03 (m, 3H), 0.94 (m, 12H), 0.69 (s, 3H).

$^{13}$C NMR (100 MHz, CDCl$_3$): δ 174.08, 104.13, 102.08, 87.91, 81.09, 71.47, 71.40, 66.00, 63.38, 55.72, 54.85, 52.55, 44.40, 43.78, 42.43, 40.14, 39.17, 37.58, 37.30, 36.85, 36.43, 35.28, 34.93, 34.67, 34.09, 31.20, 30.99, 30.83, 30.35, 29.72, 28.63, 26.91, 26.21, 24.75, 24.41, 23.40, 21.18, 20.43, 18.40, 12.96, 12.15.

Example 11

Synthesis of JZ-10

K$_2$CO$_3$ (276 mg, 2.0 mmol) and a catalytic amount of KI were added successively to a solution of 10-(2-bromoethoxy)dihydroartemisinin (391 mg, 1.0 mmol) and hyodeoxycholic acid (392 mg, 1.0 mmol) in DMF (20 mL) at room temperature. The reaction mixture was heated to 70° C. and reacted for 2 h. When the reaction was determined by TLC to be completed, water (20 mL) was slowly added to quench the reaction, and the reaction mixture was extractied with ethyl acetate (20 mL×3). The organic phases were combined, washed with water (30 mL) and saturated NaCl solution (50 mL) in sequence, dried with anhydrous MgSO$_4$ and filtered. The filtrate was rotatorily evaporated under vacuum to give a crude product, which was purified by silica gel column chromatography to give a colorless oily compound (589 mg, yield 83.7%), where an eluent was a mixture of petroleum ether and ethyl acetate in a ratio of 4:1-1:1.

$^1$H NMR (400 MHz, CDCl$_3$): δ 5.45 (s, 1H), 4.84 (d, J=3.4 Hz, 1H), 4.28-4.22 (m, 2H), 4.10-4.00 (m, 2H), 3.67-3.62 m, 2H), 2.71-2.58 (m, 1H), 2.43-2.35 (m, 2H), 2.22 (s, 1H), 2.07 (m, 1H), 1.98-1.87 (m, 4H), 1.82-1.74 (m, 4H), 1.67-1.59 (m, 8H), 1.46-1.28 (m, 15H), 1.17-1.08 (m, 6H), 0.98-0.89 (m, 12H), 0.65 (s, 3H).

$^{13}$C NMR (100 MHz, CDCl$_3$): δ 174.10, 104.12, 102.06, 87.90, 81.09, 71.60, 68.07, 66.00, 63.38, 56.14, 55.86, 52.55, 48.39, 44.40, 42.85, 39.95, 39.80, 37.58, 36.43, 35.96, 35.35, 35.55, 35.03, 34.83, 34.66, 31.19, 30.92, 30.83, 30.24, 29.20, 28.13, 26.20, 24.74, 24.41, 24.21, 23.50, 20.75, 20.42, 18.27, 12.95, 12.05.

Example 12

Synthesis of JZ-11

To a solution of compound JZ-02 (130 mg, 0.18 mmol) in pyridine (2 mL) was added pyridine-sulfur trioxide complex (180 mg, 1.13 mmol) at 0° C. Then the reaction mixture was reacted at room temperature for 6 h until the reaction was determined by TLC to be completed. 1.0 M diluted hydrochloric acid (5 mL) was slowly added to quench the reaction, and the reaction mixture was extracted with dichloromethane (10 mL×3). The organic phases were combined, washed with 1.0 M diluted hydrochloric acid (20 mL×2) and saturated NaCl solution (30 mL), dried with anhydrous $MgSO_4$ and filtered. The filtrate was rotatorily evaporated under vacuum to give a crude product, which was purified by silica gel column chromatography to give a white solid compound JZ-11 (103 mg, 70.6%), where an eluent was a mixture of dichloromethane and methanol in a ratio of 20:1-10:1.

$^1$H NMR (400 MHz, DMSO-$d_6$): δ 11.97 (s, 1H), 5.34 (s, 1H), 4.80 (d, J=3.3 Hz, 1H), 3.94 (s, 1H), 3.39 (s, 1H), 2.42-2.30 (m, 1H), 2.29-2.04 (m, 5H), 2.01-1.89 (m, 2H), 1.84-1.54 (m, 10H), 1.38 (m, 8H), 1.27 (m, 7H), 1.21-1.10 (m, 6H), 1.00 (m, 2H), 0.92-0.81 (m, 12H), 0.61 (s, 3H).

$^{13}$C NMR (100 MHz, DMSO-$d_6$): δ 175.89, 103.71, 100.13, 87.51, 80.98, 76.33, 55.29, 55.08, 44.40, 43.66, 42.24, 41.43, 37.25, 36.55, 35.28, 35.01, 34.60, 34.25, 34.15, 33.76, 31.44, 31.27, 30.94, 30.28, 29.49, 28.97, 26.13, 25.87, 24.73, 24.60, 23.74, 21.47, 20.65, 18.78, 13.40, 12.42.

Example 13

Synthesis of JZ-12

To a solution of compound JZ-08 (130 mg, 0.18 mmol) in pyridine (2 mL) was added pyridine-sulfur trioxide complex (180 mg, 1.13 mmol) at 0° C. Then the reaction mixture was reacted at room temperature for 6 h until the reaction was determined by TLC to be completed. 1.0 M diluted hydrochloric acid (5 mL) was slowly added to quench the reaction, and the reaction mixture was extracted with dichloromethane (10 mL×3). The organic phases were combined, washed with 1.0 M diluted hydrochloric acid (20 mL×2) and saturated NaCl solution (30 mL), dried with anhydrous $MgSO_4$ and filtered. The filtrate was rotatorily evaporated under vacuum to give a crude product, which was purified by silica gel column chromatography to give a white solid compound JZ-12 (112 mg, 76.8%), where an eluent was a mixture of dichloromethane and methanol in a ratio of 20:1-12:1.

$^1$H NMR (400 MHz, DMSO-$d_6$): δ 11.75 (s, 1H), 5.33 (s, 1H), 4.79 (d, J=3.3 Hz, 1H), 4.34 (s, 1H), 3.46 (d, J=10.7 Hz, 1H), 2.37 (m, 1H), 2.27-2.11 (m, 3H), 2.08-1.92 (m, 2H), 1.83-1.57 (m, 10H), 1.53-1.43 (m, 5H), 1.40-0.97 (m, 18H), 0.96-0.78 (m, 14H), 0.64 (s, 3H).

$^{13}$C NMR (100 MHz, DMSO-$d_6$): δ 177.08, 103.70, 98.99, 87.45, 81.01, 78.29, 76.61, 52.56, 48.62, 46.45, 46.07, 44.41, 42.18, 37.21, 36.54, 36.03, 35.70, 34.68, 34.50, 33.89, 32.51, 31.61, 30.89, 28.68, 27.70, 26.46, 26.12, 25.12, 24.73, 24.02, 23.79, 20.63, 17.77, 13.41, 12.73.

Example 14

Inhibitory Effect of the Dihydroartemisinin-Steroid Conjugate on Various Tumor Cells Cultured In Vitro 1. Experimental Principle Effect of the compounds prepared in the above examples on the growth of tumor cells was investigated, where the tumor cells used herein were respectively human prostate cancer cell-PC-3 cells (CRL-1435), human cervical cancer cell line-HeLa cells (CCL-2), human acute T cell leukemia cells-Jurkat cells (TIB-152), human renal clear cell adenocarcinoma-786-0 cells (CRL-1932) and human breast cancer cells-MCF7 cells (HTB-22). African green monkey kidney cells-Vero cells (CCL-81) were used as normal cells to evaluate the cytotoxic effects of the compounds. Under the intervention of such compounds, the living cells can be stained using a cell proliferation-cytotoxicity assay kit Cell Counting Kit-8 (CCK-8 solution), and the OD value was measured to reflect the survival and growth state of the cells, that is, the cell survival rate (%) and the cell growth inhibition rate (%). Finally, a compound concentration at which only half of the cells survived, i.e., $CC_{50}$, and a compound concentration at which a cell growth inhibition rate was 50%, i.e., $IC_{50}$, were respectively calculated.

2. Experimental Materials

Vero cells (CCL-81), PC-3 cells (CRL-1435), HeLa cells (CCL-2), Jurkat cells (TIB-152), 786-O cells (CRL-1932) and MCF7 cells (HTB-22) were all purchased from ATCC; DMEM, F12 medium, MEM and RPMI 1640 medium were purchased from Gibco (Life Technologies); fetal bovine serum (FBS) was purchased from Hyclone (Thermo Scientific); trypsin was purchased from Gibco (Life Technologies); CCK-8 solution was purchased from Shanghai Dojindo Chemical Technology Co., Ltd.; 96-well cell culture plate (with a transparent and flat bottom) was purchased from Corning; and SpectraMax 190 microplate reader was purchased from Molecular Devices Corporation.

3. Experimental Method

The culture solution containing 10% FBS was regarded as a complete medium. Vero cells were cultured in DMEM complete medium; PC-3 cells were cultured in F12 complete medium; Hela cells were cultured in MEM complete medium; Jurkat cells were cultured in RPMI 1640 complete medium; 786-O cells were cultured in RPMI 1640 complete medium; and MCF-7 cells were cultured in MEM complete medium. After all the cells were cultured to logarithmic growth phase, the tests were performed as follows.

The adherent cells were digested by pancreatin and suspended to directly collect cells. The cell suspension was centrifuged, and after counted, the cells were seeded in a transparent 96-well culture plate and adjusted to 5×10$^3$ cells/100 μL/well with respective complete mediums. At the same time, each plate was provided with blank wells without cells and samples and control wells with cells but without samples. The 96-well culture plates were then cultured overnight in a 37° C., 5% $CO_2$ incubator. The test compounds were added at 50 μL/well on the next day, and respective complete mediums were added at the same amount. The final concentrations of the compound samples were respectively 100 μM, 25 μM, 6.25 μM, 1.56 μM, 0.39 μM, 0.1 μM, 0.02 μM and 0.006 μM, and each concentration was repeated twice. While for the control wells and blank wells, complete mediums rather than the compound samples were added, where the complete culture medium was also added at 100 μL/well. The culture plates were incubated in a 37° C., 5% CO$_2$ incubator for 48 h. 2 h before the end of the incubation, the culture medium was removed, and complete culture medium containing 10% CCK-8 solution was added at 100 μL/well. After the incubation, the plates were measured at 450 nM using a microplate reader for OD values (650 nM was used as reference).

The $CC_{50}$ was calculated according to the survival rate (%) of Vero cells to reflect the cytotoxic effect of the compounds. The $IC_{50}$ was calculated according to the growth inhibition (%) of the tumor cells to reflect the antitumor activity of the samples.

The survival rate and the growth inhibition were calculated as follows:

cell survival rate (%)=(OD value of the sample well−OD value of the blank well)/(OD value of the control well−OD value of the blank well)×100%; and cell growth inhibition rate (%)=[1−(OD value of the sample well−OD value of the blank well)/(OD value of the control well−OD value of the blank well)]×100%

4. Experimental Results

The results of $IC_{50}$ were shown in Tables 1 and 2. It can be seen from the tables that the dihydroartemisinin-steroid conjugate can inhibit the growth of various tumor cells. The potency of these compounds is far stronger than that of the dihydroartemisinin.

TABLE 1

Inhibitory effect of dihydroartemisinin-steroid conjugate on various tumor cells

| Compounds | Tumor cells | | | | | | |
|---|---|---|---|---|---|---|---|
| | Vero $CC_{50}$ (μM) | PC3 $IC_{50}$ (μM) | Hela $IC_{50}$ (μM) | Jurkat $IC_{50}$ (μM) | 786-O $IC_{50}$ (μM) | MCF7 $IC_{50}$ (μM) | A549 $IC_{50}$ (μM) |
| JZ-1 | 13.58 | 0.63 | 0.39 | 2.15 | 0.20 | 4.13 | 0.1 |
| JZ-2 | 7.81 | 0.26 | 0.04 | 0.24 | 0.06 | 3.39 | 0.02 |
| JZ-3 | 6.55 | 0.53 | 0.22 | 0.12 | 0.034 | 1.08 | 0.01 |
| JZ-4 | 100 | 25 | 25 | 32 | 100 | 35 | 2.40 |
| JZ-5 | 100 | 100 | 100 | 45 | 100 | 56 | 3.20 |
| JZ-6 | 100 | 100 | 100 | 34 | 100 | 45 | 6.33 |
| JZ-7 | 100 | 100 | 100 | 54 | 100 | 65 | 3.70 |
| JZ-8 | 6.5 | 0.01 | 0.45 | 0.02 | 0.006 | 0.01 | 0.006 |
| JZ-9 | 20 | 1.05 | 1.36 | 0.05 | 0.11 | 0.23 | 0.28 |
| JZ-10 | 7.1 | 0.8 | 1.01 | 0.34 | 0.09 | 2.05 | 0.05 |
| Dihydroartemisinin | 5.88 | 2.02 | 1.66 | 100 | 1.10 | 100 | 2.96 |
| Taxol | 1.5 | 0.006 | 0.006 | 0.03 | 0.006 | 0.01 | 0.006 |

TABLE 2

Inhibitory effects of JZ-2 and JZ-8 on various tumor cells

| Cells | JZ-2 $IC_{50}$ (μM) | JZ-8 $IC_{50}$ (μM) | Taxol $IC_{50}$ (μM) |
|---|---|---|---|
| U87 | 0.517 | 0.200 | 0.010 |
| SW1990 | 0.517 | 0.260 | 0.010 |
| Kasumi | 0.157 | 0.157 | 0.010 |
| U2OS | 0.357 | 0.420 | 0.010 |
| OV-90 | 0.157 | 0.157 | 0.010 |
| HC7116 | 0.157 | 0.167 | 0.010 |
| DU-145 | 0.625 | 1.300 | 0.010 |
| HEPG-2 | 0.500 | 0.500 | 0.010 |
| RCC-4 | 2.500 | 0.625 | 10.000 |
| RCC4 vhl | 30.000 | 2.500 | 30.000 |
| K562 | 0.157 | 0.157 | 0.010 |
| NB4 | 0.157 | 0.157 | 0.010 |

Example 15

Anti-Cancer Effect of JZ-2 on the Xenograft Model of Human Lung Cancer Cell A549

23 BALB/c nude mice, weighing 18-22 g and aged 2-4 weeks, were used in the experiment. Each nude mouse was subcutaneously injected with human non-small cell lung cancer cells A549 (1-5×10$^6$), and when the tumor grew to 1-2 cm$^3$ (about 40 days), the 23 nude mice were randomly divided into three groups, where group 1 (9 mice) was the control group, group 2 (9 mice) was the treatment group and group 3 (5 mice) was the positive control group (paclitaxel). Mice in group 1 were each intraperitoneally injected with 20 μL of normal saline per day; mice in group 2 were each intraperitoneally injected with 10 mg/kg JZ-02 every day with a 2-day break after 7 consecutive days of administration; and mice in group 3 were each intraperitoneally injected with 10 mg/kg paclitaxel once every three days. The entire treatment lasted for 28 days, where three deaths occurred in group 1 and one death occurred in group 3, while no death was observed in group 2, indicating that JZ-02 was less toxic than paclitaxel.

Figure 1:
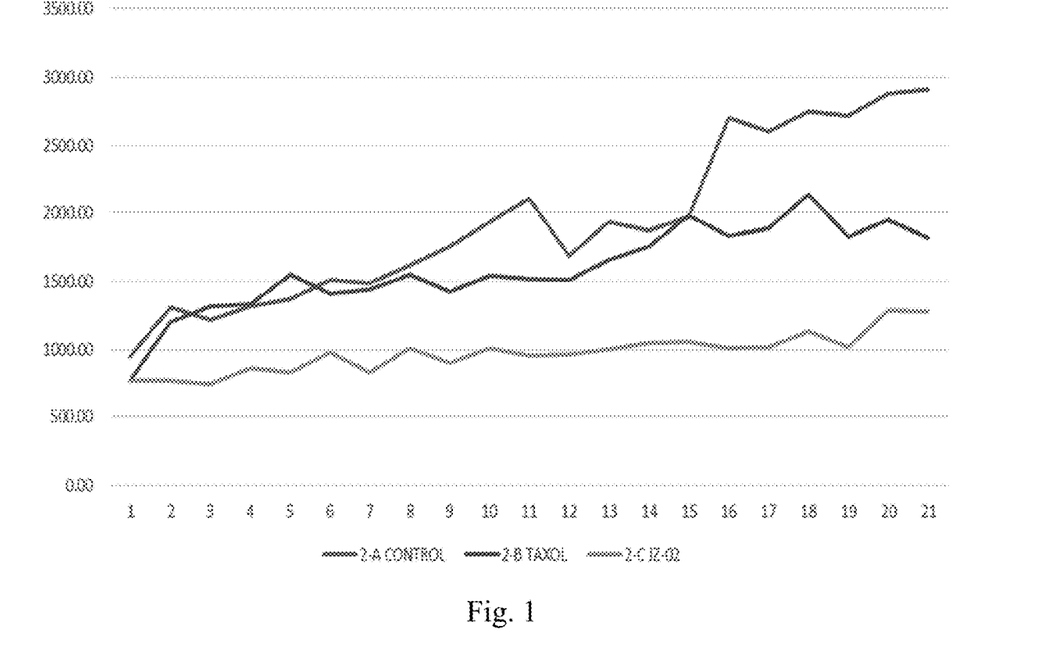
FIG. 1 is a tumor growth curve revealing an anti-cancer effect of JZ-2 prepared in Example 15 of the invention on the xenograft model of human lung cancer cell A549.

It can be seen from the tumor growth curve shown in FIG. 1 that the compound JZ-2 of the invention can significantly inhibit the tumor growth, and the inhibitory effect was better than that of the positive control paclitaxel.

Figure 2:
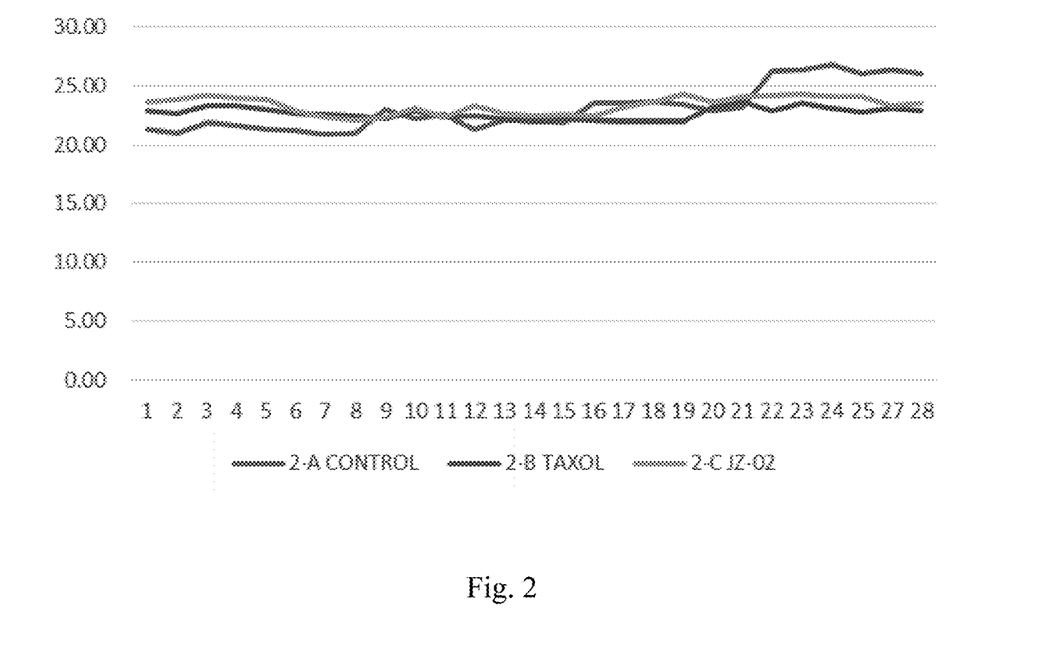
FIG. 2 is an experimental animal body weight change curve revealing the anti-cancer effect of JZ-2 prepared in Example 15 of the invention on the xenograft model of human lung cancer cell A549.

It can be seen from the body weight curve shown in FIG. 2 that there was no significant decrease in body weight of the mice after 28 consecutive days of administration of JZ-2, demonstrating that the compound was less toxic and had no significant effect on the body weight and life quality of the mice.

After the mice in each group were sacrificed, the tumor tissues were weighed for the calculation of the tumor inhibition rate, where the tumor inhibition rate of group 2 (the treatment group) was 58% and the tumor inhibition rate of the positive control group was 52%.

Described are merely preferred embodiments, which are not intended to limit the invention. It should be noted that various variations and modifications made by those skilled in the art without departing from the spirit of the invention should fall within the scope of the invention defined by the appended claims.

What is claimed is:

1. A dihydroartemisinin-steroid conjugate or a pharmaceutically-acceptable salt thereof, the dihydroartemisinin-steroid conjugate being selected from the group consisting of:

and

2. A pharmaceutical composition comprising the dihydroartemisinin-steroid conjugate of claim 1 or a pharmaceutically-acceptable salt thereof and a pharmaceutically-acceptable carrier.

3. A method of preparing the dihydroartemisinin-steroid conjugate of claim 1, comprising:
linking a hydroxyl group of dihydroartemisinin at position 10 with a hydroxyl group of the steroid compound at position 3 to form an ether bond so as to obtain the synthesizing the dihydroartemisinin-steroid conjugate.

* * * * *